(12) United States Patent
Martini

(10) Patent No.: US 11,135,099 B2
(45) Date of Patent: Oct. 5, 2021

(54) SYSTEM AND METHOD FOR TEARING OFF AND ROLLING UP A STRIP OF ABSORBENT FIBER SHEET

(71) Applicants: ONTEX BV, Buggenhout (BE); ONTEX GROUP NV, Erembodegem (BE)

(72) Inventor: Lukas Martini, Kehrig (DE)

(73) Assignees: Ontex BV, Buggenhout (BE); Ontex Group NV, Erembodegem (BE)

( * ) Notice: Subject to any disclaimer, the term of this patent is extended or adjusted under 35 U.S.C. 154(b) by 117 days.

(21) Appl. No.: 16/314,408

(22) PCT Filed: Jun. 5, 2018

(86) PCT No.: PCT/EP2018/064750
§ 371 (c)(1),
(2) Date: Dec. 29, 2018

(87) PCT Pub. No.: WO2018/224489
PCT Pub. Date: Dec. 13, 2018

(65) Prior Publication Data
US 2019/0142651 A1    May 16, 2019

(30) Foreign Application Priority Data
Jun. 7, 2017   (EP) .................................. 17174840

(51) Int. Cl.
*A61F 13/20* (2006.01)
*A61F 13/34* (2006.01)

(52) U.S. Cl.
CPC ........ *A61F 13/206* (2013.01); *A61F 13/2088* (2013.01); *A61F 13/2094* (2013.01); *A61F 13/34* (2013.01)

(58) Field of Classification Search
CPC .............. A61F 13/2094; A61F 13/2082; A61F 13/206; A61F 13/15699; A61F 13/2088;
(Continued)

(56) References Cited

U.S. PATENT DOCUMENTS

| 704,472 A | * | 7/1902 | Dear | ...................... B65H 39/06 270/59 |
| 2,129,842 A | * | 9/1938 | Holweg | .................. B31B 70/00 493/234 |

(Continued)

FOREIGN PATENT DOCUMENTS

| EP | 3165471 A1 | 5/2017 |
| GB | 2039265 A | 8/1980 |
| WO | 2017115337 A1 | 7/2017 |

OTHER PUBLICATIONS

Extended European Search Report for App. No. 17174840.3; dated Oct. 20, 2017.
(Continued)

*Primary Examiner* — Anna K Kinsaul
*Assistant Examiner* — Veronica Martin
(74) *Attorney, Agent, or Firm* — VIVICAR Law, PLLC

(57) ABSTRACT

A system and method for tearing off and rolling up a strip of absorbent fiber sheet for a tampon are discussed. An endless absorbent fiber sheet is propagated with a first linear speed by a first pair of rolls, and with at least the first linear speed by a second pair of rolls. A pulling means is provided to induce a second linear speed in the sheet larger than the first linear speed for tearing off a strip from the sheet. The first pair of rolls is configured to maintain the first linear speed of the absorbent fiber sheet, while the second pair of rolls is configured to rotate in a freewheel-type manner when the absorbent fiber sheet is pulled through the second pair of rolls at linear speeds larger than the first linear speed.

(Continued)

Preferably, the pulling means is a rotatable clamping means for rolling up the strip.

5 Claims, 4 Drawing Sheets

(58) Field of Classification Search
CPC ... A61F 13/34; B65H 2513/106; B65H 35/10; B31B 70/14; B31B 70/146; B31B 70/16; B31B 70/20
USPC .......................................................... 493/369
See application file for complete search history.

(56) References Cited

U.S. PATENT DOCUMENTS

| | | | |
|---|---|---|---|
| 2,380,949 A | 8/1945 | Davidson | |
| 2,902,197 A * | 9/1959 | Potdevin | B65H 35/10 225/105 |
| 3,203,323 A * | 8/1965 | Adams | B31B 70/00 493/234 |
| 3,561,332 A * | 2/1971 | Ross | B31B 70/00 493/63 |
| 3,688,346 A | 9/1972 | Johst et al. | |
| 4,816,100 A * | 3/1989 | Friese | A61F 13/2085 156/191 |
| 5,084,038 A * | 1/1992 | Sheldon | A61F 13/2082 156/193 |
| 5,141,142 A * | 8/1992 | Ramsey | B65H 35/10 225/100 |
| 5,407,513 A * | 4/1995 | Hayden | A61F 13/15756 156/265 |
| 5,785,224 A * | 7/1998 | Nowakowski | B65H 35/10 225/100 |
| 6,550,517 B1 * | 4/2003 | Hilt | B65C 1/02 156/517 |
| 6,763,749 B2 * | 7/2004 | Droste | B65H 20/24 156/164 |
| 7,059,505 B2 * | 6/2006 | Tabor | B65H 35/10 156/250 |
| 7,712,287 B2 * | 5/2010 | Gallimore | B65B 61/20 53/435 |
| 7,874,509 B2 * | 1/2011 | Kenney | A47K 10/3612 242/563.2 |
| 8,062,459 B2 * | 11/2011 | Nakakado | B65H 20/04 156/256 |
| 8,673,098 B2 * | 3/2014 | McCabe | A61F 13/15593 156/163 |
| 8,839,836 B2 * | 9/2014 | Cocozzella | B65H 39/14 156/519 |
| 8,845,837 B2 | 9/2014 | Tomsovic et al. | |
| 10,517,772 B2 * | 12/2019 | Heege | B32B 37/22 |
| 2010/0130907 A1 * | 5/2010 | Linkel | A61F 13/2065 604/11 |
| 2013/0036584 A1 * | 2/2013 | Ishikawa | A61F 13/2085 28/118 |
| 2013/0040796 A1 * | 2/2013 | Thies | B23K 26/382 493/239 |
| 2014/0115845 A1 * | 5/2014 | Tomsovic | A61F 13/2068 28/118 |
| 2014/0115847 A1 * | 5/2014 | Tomsovic | A61F 13/206 28/118 |
| 2018/0319115 A1 * | 11/2018 | Fichtner | B31B 70/876 |
| 2019/0008697 A1 * | 1/2019 | Heege | A61F 13/15699 |

OTHER PUBLICATIONS

International Search Report and Written Opinion for PCT/EP2018/064750; dated Aug. 2, 2018.

* cited by examiner

SYSTEM AND METHOD FOR TEARING OFF AND ROLLING UP A STRIP OF ABSORBENT FIBER SHEET

CROSS-REFERENCE TO RELATED APPLICATIONS

This application is the national stage application of corresponding international application number PCT/EP2018/064750, filed Jun. 5, 2018, which claims priority to and the benefit of European application no. 17174840.3, filed Jun. 7, 2017, all of which are hereby incorporated by reference in their entirety.

TECHNICAL FIELD

The invention pertains to the technical field of tampon manufacturing. More in particular, the invention describes a system and a method for tearing off and rolling up a strip of absorbent fiber sheet. The rolled-up strip can be used as a tampon blank for pressing a tampon in a subsequent pressing step or apparatus.

BACKGROUND

Tampons are well known in the art and are used for feminine hygiene. Also many tampon manufacturing methods and apparatuses have been disclosed in the prior art. Document U.S. Pat. No. 8,845,837 discloses an example. Generally, a distinction is made between folded and rolled tampons. The former are commonly used with an applicator to reduce the chance of tears and other damage to the tampon. Rolled tampons usually have superior longitudinal strength over folded tampons. Hence, most rolled tampons can be applied digitally, although they can also be used in combination with an applicator. Rolled tampons comprise a rolled absorbent fiber sheet and a withdrawal string for removal. The rolled absorbent fiber sheet comprises an insertion end, a withdrawal end, and an essentially cylindrical body in between. The withdrawal string extends out of the withdrawal end. Sometimes rolled tampons also comprise a cover of a nonwoven, encapsulating the cylindrical body.

Rolled tampons can be manufactured by in-line processing of a continuous or endless absorbent fiber sheet. The endless absorbent fiber sheet is propagated, a piece of the sheet is detached, and the piece is subsequently rolled up. The piece can comprise a nonwoven film and a string looped around the piece. A weakened division line can be applied to the absorbent fiber sheet to facilitate detachment, and to determine the location of bursting. Detachment itself can be performed by applying a pulling force to the absorbent fiber sheet which is mediated by the absorbent sheet to the weakened division line, where it causes bursting. During in-line processing, it is important to limit the mediation of the pulling force to a single weakened division line.

Prior to the present invention, the inventors used a carousel of clamps for detachment. A first and a second clamp grasp the endless absorbent fiber sheet, one clamp on each side of the weakened division line, the first clamp grasping the piece to be detached. When the carousel moves the first clamp faster than the second clamp, tension is built over the weakened division line, and the pulling force causes bursting of the weakened division line. The first clamp brings the detached piece to a rolling fork, the fork comprising two longitudinal prongs, the detached piece entering the fork in between the two longitudinal prongs. The fork is then rotated about an axis in essence parallel to the longitudinal prongs, rolling up the detached piece to a tampon preform. The carousel involves several moving components such as the carousel band and the clamps which can be opened and closed and which make loops with the carousel. Because there are multiple moving components, the carousel is prone to mechanical defect. In addition, multiple clamps are required to perform the detachment, and the detachment and rolling up of the piece occur at different components of the in-line processing machine. A further disadvantage is the difficulty to position the detached piece accurately with respect to the two longitudinal prongs, as the detached piece is briefly suspended in air in between opening the carrying clamp and rotating the fork.

U.S. Pat. No. 2,380,949 discloses a severing apparatus for progressively dividing a continuous strip of material into a succession of individual sheets upon longitudinally spaced transverse weakened division lines by subjecting succeeding terminal portions of the strip to longitudinal pulling strain in excess of the tensile strength of the strip coincident with such weakened lines, including a pair of tensioning rollers and a pair of snubbing rollers rotating at different peripheral speeds, strip feeding means for advancing the strip in synchronism with the rotation of the rollers to position a transverse weakened line of the strip intermediate the respective pairs of rollers preparatory to succeeding strip gripping actions thereof, and common operating means for intermittently shifting the strip feeding means and the rollers of the respective pairs toward and from coating rollers of the pairs to simultaneously grip an intermediate strip of material at opposite sides of a transverse weakened line thereof.

A first disadvantage of the severing apparatus disclosed in U.S. Pat. No. 2,380,949 is the need to provide strip feeding means separately from the rollers, as the latter are intermittently lifted and only used for detachment. A second disadvantage is the need, in addition to the enclosed severing apparatus, of a distinct mechanism for rolling up the detached pieces to tampon preforms.

US 2014/0,115,847 discloses a method of manufacturing a tampon. A method of manufacturing a tampon generally comprises forming a softwind including a core and a cover overlying and at least in part covering the core. The cover carries an absorbent web having a free end and a bonded end wherein the free end is capable of moving relative to the cover. The softwind is passed through a transfer assist device to facilitate the transferring of the free end of the absorbent web without the absorbent web becoming misaligned relative to the cover.

In an embodiment, US 2014/0,115,847 discloses a pair of opposed conveyors to move the main ribbon. A winding and sealing device is configured to separate the web about the line of weakness into individual units as the web is being fed to the winding and sealing device.

A disadvantage of the apparatus disclosed in US 2014/0,115,847 is the lack of (active or passive) means to guide the front end of the thorn absorbent web from the opposed conveyors to the winding and sealing device. The absorbent web will bend and hang due to gravity. Furthermore, the absorbent web can easily get stuck and accumulate when being pushed instead of pulled. Providing merely passive guiding means is therefore insufficient to propagate the front end of the thorn absorbent web from the opposed conveyors to the winding and sealing device.

The present invention aims to resolve at least some of the problems mentioned above.

SUMMARY OF THE INVENTION

In a first aspect, the present invention pertains to a method of making a tampon. The method comprises the steps of:

providing an endless absorbent fiber sheet along a machine direction;

optionally providing breakage lines to said endless sheet essentially along a cross direction perpendicular to said machine direction;

frictionally pulling on the sheet with a first linear speed at a first position along the machine direction;

frictionally pulling on the sheet with essentially at least the first linear speed at a second position along the machine direction, said second position being downstream of the first position with respect to the machine direction;

tearing off a strip of absorbent fiber sheet from the endless sheet by pulling on the sheet at a third position along the machine direction, said third position being downstream of the first and second position with respect to the machine direction, said pulling inducing a second linear speed on the sheet at the third position which is larger than said first linear speed, thereby inducing an effective tearing force on the sheet between the first and the third position, rolling up the strip of absorbent fiber sheet, characterized in that at the first position the first linear speed of the sheet is essentially maintained and that at the second position the sheet is allowed to obtain a speed at the second position which is higher than the first linear speed when the sheet is being pulled at the third position.

In a second aspect, the present invention pertains to a system for making a tampon. The system comprises a first pair of rolls, a second pair of rolls, and a pulling means. The system is adapted to propagate an endless absorbent fiber sheet from the first pair of rolls to the second pair of rolls and from the second pair of rolls to the pulling means. The first pair of rolls is mounted on a first frame with a distance in between the first pair of rolls smaller than the thickness of the absorbent fiber sheet. The second pair of rolls is mounted on the first or a second frame with a distance in between the second pair of rolls smaller than the thickness of the absorbent fiber sheet. The distances in between the first and the second pair of rolls are thereby suitable for clamping the absorbent fiber sheet. The first pair of rolls is configured to rotate and thereby frictionally pull the endless absorbent fiber sheet with a first linear speed. The second pair of rolls is configured to rotate and thereby pull the endless absorbent fiber sheet with essentially the first linear speed. The pulling means are configured to intermittently pull the absorbent fiber sheet with a second linear speed larger than the first linear speed for tearing off a strip from the endless absorbent fiber sheet. The system is characterized in that the first pair of rolls is configured to essentially maintain the first linear speed at the contact position with the absorbent fiber sheet and that the second pair of rolls is configured to rotate in a freewheel-type manner when the absorbent sheet is pulled through the second pair of rolls at linear speeds larger than the first linear speed.

The system and method for making a tampon are advantageous for several reasons.

The number of moving parts is limited. The first and the second pair of rolls have a fixed position and their movement is restricted to rotation. Both pairs of rolls thereby remain in contact with a passing absorbent fiber sheet. Both pairs of rolls not only fulfil the function of propagating the absorbent fiber sheet, but also aid in the step of tearing off a strip. The first pair of rolls maintains the first linear speed (at the first position). A pulling force exerted by the pulling means (at the third position) is thereby not mediated beyond the first pair of rolls (at the first position) and only the weakened division line in between the first pair of rolls (at the first position) and the pulling means (at the third position) feels the pulling force induced by the pulling means (at the third position). The second pair of rolls is configured to rotate in a freewheel-type manner when the pulling means induces the second linear speed in the absorbent fiber sheet. The pulling force can thereby be freely propagated from the pulling means (third position) over the second pair of rolls (second position) to a weakened division line in between both pairs of rolls (first and second position).

In a preferred embodiment of the system, the pulling means comprises rotatable clamping means. In a preferred embodiment of the method, at the third position the fiber sheet is being pulled by clamping the sheet by rotatable clamping means and rotating the clamped sheet at a rotational speed which induces said second linear speed on the sheet.

The rotatable clamping means fulfil the dual purpose of tearing off a strip from the endless absorbent fiber sheet and rolling up the strip. As the rotatable clamping means clamps the endless absorbent fiber sheet prior to detachment of a strip and roll-up due to rotation of the rotatable clamping means, the strip is never suspended in air, not does clamping or rotation without clamping occur after detachment. The positioning of the strip with respect to the rotatable clamping means can therefore be controlled to a much higher degree, and the positioning is therefore substantially more accurate.

In the figures and the detailed description, preferred embodiments of the present invention are described in detail.

DETAILED DESCRIPTION OF THE INVENTION

Figure 1:
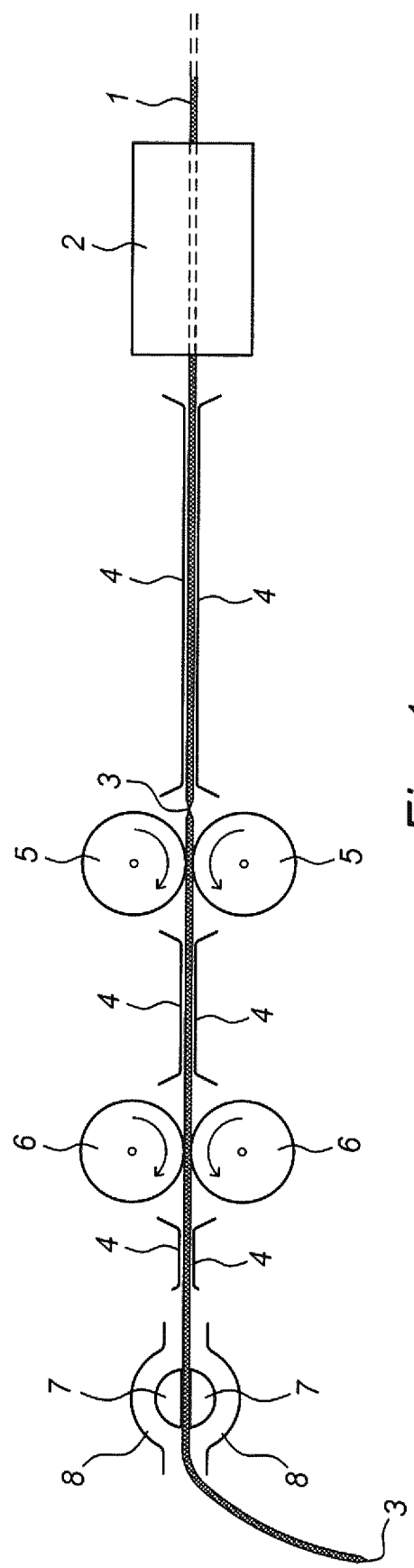
FIGS. 1, 2 and 4 schematically represent preferred embodiments of systems according to the present invention, and the in-line processing of an endless absorbent fiber sheet with the system.

The present invention concerns a system and a method for tearing off and rolling up an absorbent fiber sheet.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Absorbent fiber sheet" as used herein refers to a sheet suitable for manufacturing of a tampon absorbent body, comprising loosely connected fibers of materials such as cotton, rayon (also called viscose), polyester, polyethylene, polypropylene or blends of any of said materials or of a combination of fibers of any of said fiber materials. For example an "absorbent fiber sheet" could consist essentially of 50% cotton fibers and 50% rayon fibers whereby both of these fibers are pressed into one loose sheet. In another example an "absorbent fiber sheet" could consist essentially of 100% rayon pressed into one loose sheet. In another example an "absorbent fiber sheet" could consist essentially of 95% rayon fibers and a 5% of fibers of a thermoplastic blend pressed into one loose sheet.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

"Structurally similar pulling means" as used herein refers to a pulling means which comprises a pulling mechanism identical, to the pulling means it is referring to. For example a pulling means comprising the pulling mechanism of a rotatable clamping means would be considered "structurally similar" to another pulling means comprising a rotatable clamping means. In another example a pulling means comprising the pulling mechanism of a carousel of clamps would be considered "structurally similar" to another pulling means comprising a carousel of clamps.

The recitation of numerical ranges by endpoints includes all numbers and fractions subsumed within that range, as well as the recited endpoints.

FIG. 1 schematically represents a preferred embodiment of a system for tearing off (bursting, tugging) and rolling up a strip of absorbent fiber sheet according to the present invention. In a preferred embodiment, the strip can comprise one or more nonwoven films and/or one or more strings looped around the strip.

An endless absorbent fiber sheet 1 is propagated by the system in a machine direction parallel to the absorbent fiber sheet. A person skilled in the art will appreciate that the machine direction may vary along the system. The machine direction is therefore a local concept. The machine direction is typically parallel to the local speed (also referred to as velocity vector) of the absorbent fiber sheet. This local speed is typically parallel to the portion of absorbent fiber sheet under consideration.

Weakened division lines 3 are applied to the endless absorbent fiber 1 sheet with a means for applying weakened division lines 2. Weakened division lines 3 can be applied by cutting, perforating, stretching, scratching such as with the use of a die cutter or a knife cutter, and the like. Weakened division lines 3 can also be applied by chemical treatment such as the application of acid or thermal treatment such as a heating, partial burning or freezing. The weakened division lines 3 are preferably applied in a cross direction perpendicular to the machine direction. Preferably, the weakened division lines 3 are spaced on the endless absorbent fiber sheet 1 at regularly spaced intervals along the machine direction. During in-line processing, the application of a nonwoven film to the absorbent fiber sheet can occur before or after application of weakened division lines 3. Similarly, the application of a string looped around the absorbent fiber sheet can occur before or after application of the weakened division lines 3. Preferably, the system comprises to this end a detachment means for detaching a nonwoven strip from an endless sheet of nonwoven film; a bonding installation for at least partially attaching said nonwoven strip to the absorbent fiber sheet; a looping means for looping a string around the absorbent fiber sheet; and a cutting means for detaching a piece of string.

The system further comprises a first pair of rolls 5 mounted on a first frame with a distance in between the first pair of rolls smaller than the thickness of the absorbent fiber sheet 1. The second pair of rolls 6 is mounted on the first or a second frame with a distance in between the second pair of rolls smaller than the thickness of the absorbent fiber sheet 1. The distances in between the pairs of rolls 5, 6 are thereby suitable for clamping the absorbent fiber sheet 1. The first pair of rolls 5 is configured to rotate and thereby frictionally pull the endless absorbent fiber sheet 1 with a first linear speed. The second pair of rolls 6 is configured to rotate and thereby pull the endless absorbent fiber 1 sheet with essentially the first linear speed. The rolls can thereby be driven by at least one motor.

During in-line processing, the absorbent fiber sheet 1 is propagated from the first pair of rolls 5 to the second pair of rolls 6. From the second pair of rolls 6, the absorbent fiber sheet 1 is propagated to a pulling means. Preferably, the pulling means comprises a rotatable clamping means 7 for clamping the endless absorbent fiber sheet and for tearing off and rolling up a strip of absorbent fiber sheet. The tearing off and rolling up of the strip are thereby performed by the same rotational motion of the rotatable clamping means 7. When a nonwoven film and string have been applied, the absorbent fiber strip is rolled up so that the nonwoven film is located on an outer side of the rolled-up absorbent fiber strip and that the string extends from a longitudinal end of the rolled-up strip.

In a preferred embodiment of the present invention, the system comprises guiding means 4 to guide the absorbent fiber sheet 1 to the first pair of rolls 5 and/or from the first pair of rolls 5 to the second pair of rolls 6 and/or from the second pair of rolls 6 to the rotatable clamping means 7. Preferably the guiding means 4 comprise one or more pairs of guiding blades 4, each pair of blades 4 comprising a slit to guide the absorbent fiber sheet 1 in between the blades. The slit of each pair of guiding blades 4 is thereby thin enough for limiting substantial movement of the sheet 1 in a direction perpendicular to the sheet 1.

In a preferred embodiment, the rotatable clamping means comprises a cylindrical casing 8, the cylindrical casing 8 comprising two slits to let through the absorbent fiber sheet 1. The cylindrical casing 8 is suitable for spatially restricting a rolled-up tampon preform to prevent it from unrolling during and/or after the rolling up step.

In a particular preferred embodiment the guiding blades 4 between the second pair of rolls 6 and the rotatable clamping means 7 are movable and configured to move into the cylindrical casing 8 and essentially into contact with the rotatable clamping means 7 while the absorbent fiber sheet 1 is guided towards and through the clamping means 7. The guiding blades 4 will move backwards to their initial position before the rolling up step.

Figure 2:
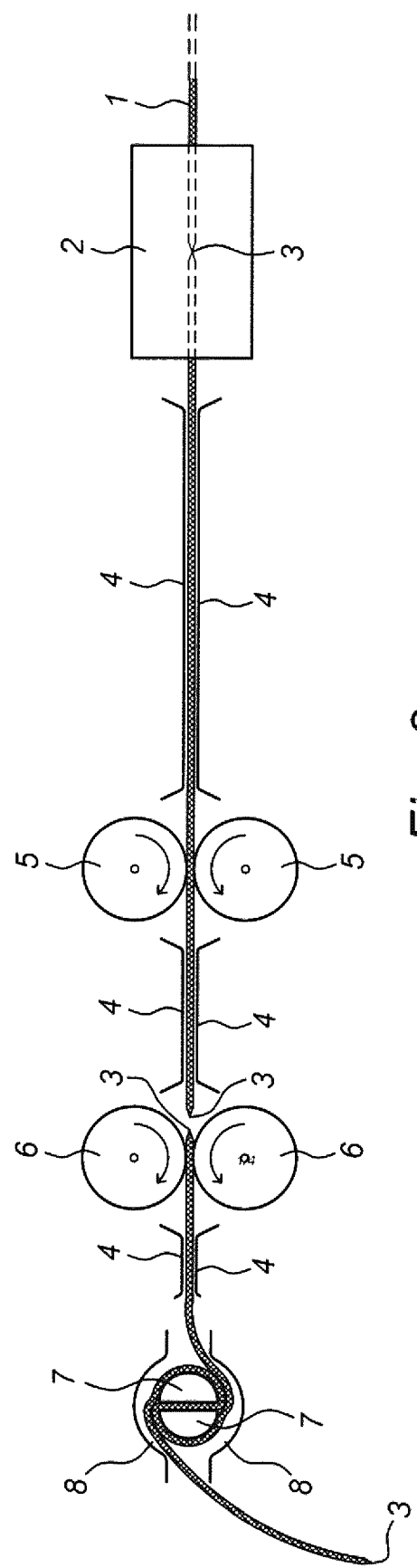
Figure 3:
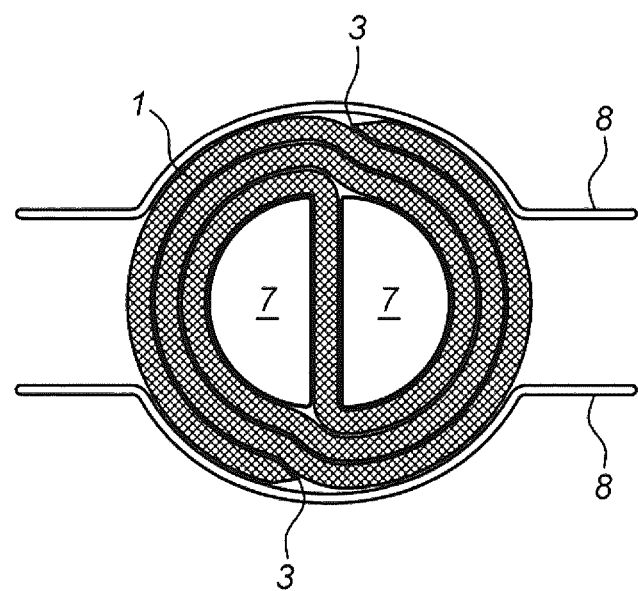
FIG. 3 schematically represents a preferred embodiment of a rotatable clamping means according to the present invention and a strip of absorbent fiber sheet rolled-up to a tampon preform.

We now turn to FIG. 2. When a weakened division line 3 is in the region in between the first pair of rolls 5 and the second pair of rolls 6, the rotatable clamping means 7 clamps and rolls up the endless absorbent fiber sheet 1. The rotation induces a second linear speed on the absorbent fiber sheet 1 larger than the first linear speed and thereby exerts a pulling force on the endless absorbent fiber sheet 1. The first pair of rolls 5 limits the linear speed of the absorbent fiber sheet 1 to at most the first linear speed. The second pair of rolls 6 can passively rotate, i.e. rotate in a freewheel-type manner, when an external force induces a linear speed larger than the first linear speed in the absorbent fiber sheet 1. The pulling force due to the rotatable clamping means is therefore mediated by the absorbent fiber sheet 1 to the weakened division line 3 in between both pairs of rolls 5, 6. The first pair of rolls 5 prevents the further mediation of the pulling force along the absorbent fiber sheet 1 beyond the first pair of rolls 5. The pulling force causes bursting along the weakened division line 3 and the detached strip of absorbent fiber web is spirally rolled up to a tampon preform. The cylindrical casing 8 of the rotatable clamping means thereby prevents expansion of the spirally rolled-up tampon preform. FIG. 3 is a schematic representation of a rotatable clamping means 7 comprising a spirally rolled-up tampon preform.

Figure 4:
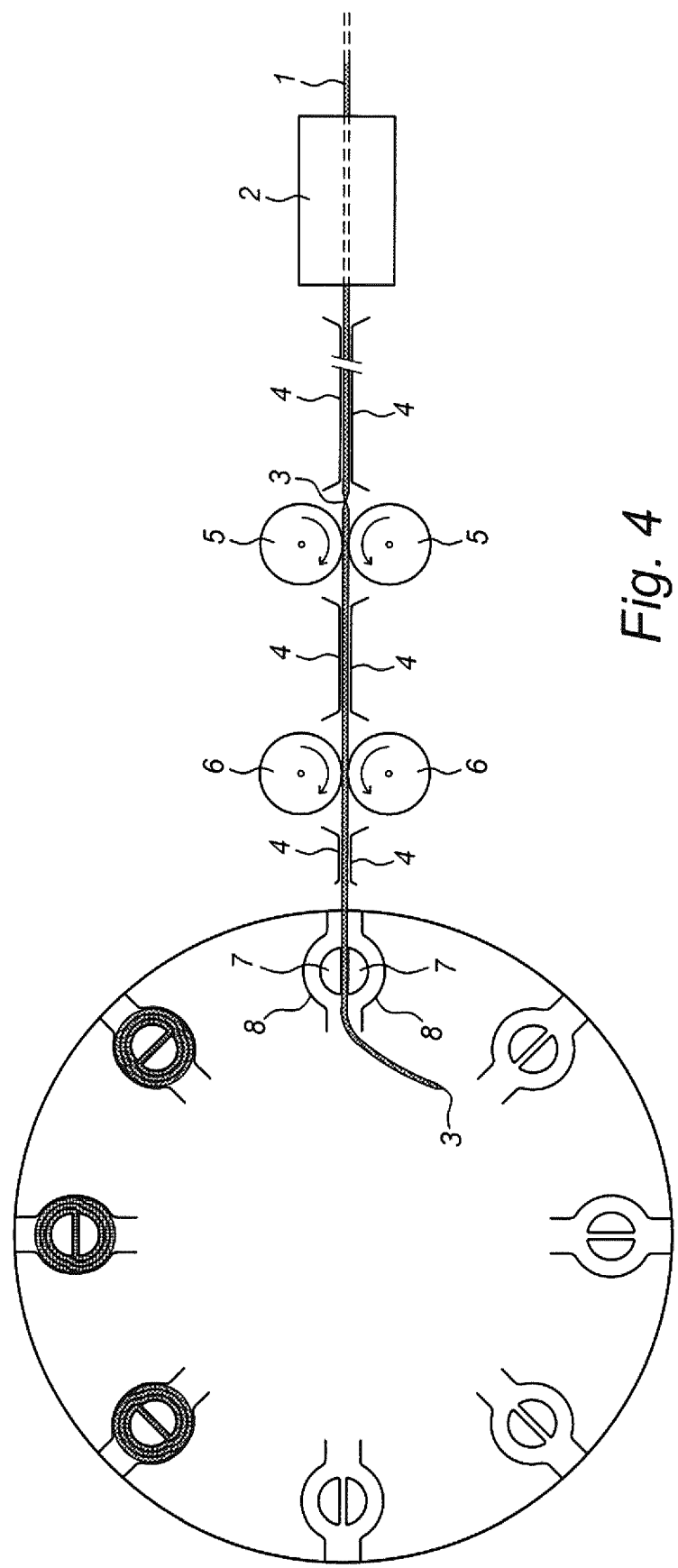

Once a spirally rolled-up tampon preform is formed on the rotatable clamping means, either the tampon preform should be removed from the clamping means or another rotatable clamping means should be provided, before the new tip of the propagated endless absorbent fiber sheet arrives. FIG. 4 schematically represents a preferred embodiment of the system of the present invention. The system comprises a wheel for conveying an at least partially rolled-up strip away from the endless absorbent fiber sheet, the wheel comprising a wheel axis in essence parallel to the transversal direction about which the wheel can be rotated. The wheel in FIG. 4 comprises eight rotatable clamping means. Each rotatable clamping means comprises a cylindrical casing for limiting the expansion of a spirally rolled-up detached strip of absorbent fiber sheet. The specific embodiment in FIG. 4 should not be interpreted as limiting. The wheel can comprise any number of rotatable clamping means larger than or equal to two rotatable clamping means, preferably at least four rotatable clamping means, more preferably at least six rotatable clamping means. When a first strip of absorbent fiber sheet arrives at a first rotatable clamping means, it passes through the slit of the first rotatable clamping means. This slit is adjusted to clamp the absorbent fiber sheet when the weakened division line enters the region in between the first pair of rolls 5 and the second pair of rolls 6. After clamping, preferably shortly or immediately after clamping, the first rotatable clamping means starts to rotate. The rotating clamping means induces via the second pair of rolls which rotate in a freewheel-type manner a pulling force over the weakened division line, which causes the weakened division line to burst and the detached strip of absorbent fiber sheet to be rolled up to a spirally wound tampon preform. The wheel is rotated, in FIG. 4 counterclockwise from the viewing perspective in FIG. 4, but in another embodiment the rotation can be clockwise. A second rotatable clamping means is thereby positioned, with its slit accordingly adjusted, to receive the new tip of the absorbent fiber sheet, and the process is repeated. The spirally rolled-up tampon preform in and around the first rotatable clamping means is removed for further processing from the first rotatable clamping means at a position which is different from the receiving position for the tip of the endless absorbent fiber sheet.

The invention is further described by the following non-limiting example which further illustrates the invention, and is not intended to, nor should it be interpreted to, limit the scope of the invention.

EXAMPLE

This example describes the manufacturing of rolled tampons by in-line processing. An endless absorbent fiber sheet is formed out of a web of fiber. The endless absorbent fiber sheet is locally propagated in a machine direction parallel to the absorbent fiber sheet. The endless absorbent fiber sheet also comprises a cross direction parallel to the absorbent fiber sheet and orthogonal to the machine direction. It can occur that the machine direction changes during in-line processing, for example when the endless absorbent fiber sheet is led over a pulley of some sort. Typically the cross direction remains in essence invariant throughout a large part of the manufacturing process, until a strip of absorbent fiber web is detached and rolled up. After detachment and roll-up, the tampon preform can of course move freely with respect to the propagating endless absorbent fiber sheet. The width of the absorbent fiber sheet as measured along the cross direction, i.e. the distance between the two parallel edges, is at least 2 cm and at most 15 cm, more preferably at least 3 cm and at most 11 cm, even more preferably at least 4 cm and at most 7 cm, such as 4 cm, 4.5 cm, 5 cm, 5.5 cm, 6 cm, 6.5 cm, 7 cm, or any value in between.

The endless absorbent fiber sheet is propagated for in-line processing. A roll of nonwoven film comprising thermoplastic fibers is unrolled and propagated as well. The nonwoven film also comprises two parallel edges, and a cross direction. The nonwoven film is cut at regularly spaced intervals along lines in essence parallel to its cross direction, and the detached strips of nonwoven film are applied onto the endless absorbent fiber sheet. Weakened division lines in essence parallel to the transversal direction are perforated in the absorbent fiber sheet at regularly spaced intervals. A roll of string is unrolled, looped around the endless absorbent fiber sheet, thereby comprising on either side of the absorbent fiber sheet a string path extending between the two parallel edges of the absorbent fiber sheet, and cut. The endless absorbent fiber sheet comprising one or more nonwoven films, one or more strings looped around the absorbent fiber sheet, and one or more weakened division lines is led trough a first pair of rolls. The first pair of rolls is at all times in contact with the absorbent fiber sheet. The first pair of rolls at all times clamps the absorbent fiber sheet and its rolls are rotating and thereby propagating the absorbent fiber sheet with a first linear speed. The first pair of rolls at all times limits the linear speed of the absorbent fiber sheet at that point of the in-line process to essentially the first linear speed. The first linear speed can be equal to the linear speed of the absorbent fiber sheet in the prior elements and/or prior steps of the in-line process. Preferably, the first linear speed is slightly larger than the linear speed of the absorbent fiber sheet in the prior elements and/or steps of the in-line process, to slightly tension the absorbent fiber sheet. The endless absorbent fiber sheet is led by a pair of guiding blades from the first pair of rolls to and through a second pair of rolls. The second pair of rolls clamps the absorbent fiber sheet and its rolls are rotating and thereby propagating the absorbent fiber sheet at essentially the first linear speed. The second pair of rolls are adapted to rotate passively, i.e. in a freewheel-type manner, when an absorbent fiber sheet is pulled through the second pair of rolls at a linear speed larger than the first linear speed. From the second pair of rolls, the absorbent fiber sheet is led to a particular rotatable clamping means, the particular rotatable clamping means mounted on a rotatable wheel comprising multiple rotatable clamping means, whereby the guiding blades between the second pair of rolls and the rotatable clamping means are moved forward in essentially contact with the rotatable clamping means. Each rotatable clamping means comprises a cylindrical casing for spatially restricting a rolled-up tampon preform to prevent it from unrolling during and/or after the rolling up step. The tip of the endless absorbent fiber sheet is led trough the slit of the particular rotatable clamping means and the guiding blades are moved backwards into their initial position. When a weakened division line is in the region in between the first pair and the second pair of rolls, the slit is adjusted to clamp the passing absorbent fiber sheet and the clamping means starts to rotate. The rotation of the clamping means induces locally a second linear speed on the absorbent fiber sheet larger than the first linear speed. Thereby the rotation of the clamping means induces a pulling force on the endless absorbent fiber sheet, which is mediated by the then passively rolling second pair of rolls to the weakened division line. The rest of the absorbent fiber sheet continues to propagate at the first linear speed, as the first pair of rolls limits the rest of the absorbent fiber sheet thereto. Tension is built over the weakened division line, the absorbent fiber sheet bursts at the weakened division line, and the detached strip of absorbent fiber sheet is pulled through the then passively rotating second pair of rolls. The rotation of the clamping means simultaneously exerts a pulling force and rolls up the strip of absorbent fiber sheet.

The system and the spatial separation of consecutive weakened division lines are adapted to clamp the endless absorbent fiber sheet at a clamping line in essence parallel to the cross direction, the clamping line in essence at a central position in between, and therefore at an equal distance from, the tip of the endless absorbent fiber sheet and the weakened division line. The rotating clamping means rolls up the detached strip of absorbent fiber sheet to a spiral form with two spiral arms. Preferably the two spiral arms are equally long. A casing around the rotatable clamping means limits the radial expansion of the spirally rolled-up tampon preform. The wheel rotates to move away the tampon preform and to bring an empty rotatable clamping means for receiving the new tip of the endless absorbent fiber sheet. The tampon preform is brought to a compressing means to radially compress the tampon preform and potentially apply grooves. The rolled tampons are then individually packaged.

The invention claimed is:

1. Method for tearing off and rolling up a strip of absorbent fiber sheet (1) for a tampon, comprising the steps of
   providing a continuous absorbent fiber sheet (1) along a machine direction;
   providing weakened division lines (3) to said absorbent fiber sheet (1) along a cross direction perpendicular to said machine direction;
   frictionally pulling on the absorbent fiber sheet (1) by a first pair of rollers (5) with a first linear speed at a first position along the machine direction;
   frictionally pulling on the absorbent fiber sheet (1) by a second pair of rollers (6) with at least the first linear speed at a second position along the machine direction, said second position being downstream of the first position with respect to the machine direction;
   guiding the absorbent fiber sheet (1) by one or more movable guiding means (4) towards a third position, said third position being downstream of the first and second position with respect to the machine direction;
   bursting the weakened division lines (3), thereby producing a strip of absorbent fiber sheet from the absorbent fiber sheet (1), by pulling on the absorbent fiber sheet (1) at the third position along the machine direction, said pulling inducing a second linear speed on the absorbent fiber sheet (1) at the third position which is larger than said first linear speed, thereby inducing an effective tearing force on the absorbent fiber sheet between the first and the third position,
   rolling up the strip of absorbent fiber sheet,
   characterized in that at the first position the absorbent fiber sheet (1) is essentially maintained at the first linear speed and that at the second position the absorbent fiber sheet (1) is allowed to obtain a speed at said second position which is higher than the first linear speed when the absorbent fiber sheet is being pulled at the third position,
   characterized in that at the third position the absorbent fiber sheet (1) is being pulled by:
   clamping the absorbent fiber sheet (1) by rotatable clamping means (7); and
   rotating the clamped absorbent fiber sheet (1) at a rotational speed which induces said second linear speed on the absorbent fiber sheet (1).

2. Method according to claim 1, characterized in that the method comprises the steps of:
   a. providing a nonwoven film and a string;
   b. applying the nonwoven film onto the absorbent fiber sheet (1) upstream of the first position with respect to the machine direction; and
   c. looping the string around the absorbent fiber sheet (1) upstream of the first position with respect to the machine direction,
   whereby the strip of absorbent fiber sheet is rolled up with the nonwoven film on an outer side of the rolled-up strip of absorbent fiber sheet and the string extending from a longitudinal end of the rolled-up strip of absorbent fiber sheet.

3. Method according to claim 1, characterized in that the method comprises the step of limiting the movement of the absorbent fiber sheet (1) in a direction perpendicular to the absorbent fiber sheet (1):
   a. from a location downstream of the first position with respect to the machine direction to a location upstream of the second position with respect to the machine direction; and/or
   b. from a location downstream of the second position with respect to the machine direction to a location upstream of the third position with respect to the machine direction.

4. Method according to claim 1, characterized in that the method comprises the step of spatially restricting the rolled-up strip of absorbent fiber sheet to restrain said absorbent fiber sheet (1) from unrolling during and/or after the rolling up step.

5. Method according to claim 1, characterized in that the effective tearing force on the absorbent fiber sheet is induced between the first and the second position.

* * * * *